US012736538B2

(12) United States Patent
Fujiura et al.

(10) Patent No.: US 12,736,538 B2
(45) Date of Patent: Sep. 15, 2026

(54) COMPOSITION FOR CANCER CELL ADHESION, CANCER CELL COLLECTION FILTER, AND METHOD FOR DETECTING CANCER CELL

(71) Applicants: MARUZEN PETROCHEMICAL CO., LTD., Tokyo (JP); KYUSHU UNIVERSITY, NATIONAL UNIVERSITY CORP., Fukuoka (JP)

(72) Inventors: Kento Fujiura, Ichihara (JP); Tomoya Ueda, Fukuoka (JP); Masaru Tanaka, Fukuoka (JP)

(73) Assignees: Maruzen Petrochemical Co., LTD., Tokyo (JP); Kyushu University, National University Corporation, Fukuoka (JP)

( * ) Notice: Subject to any disclaimer, the term of this patent is extended or adjusted under 35 U.S.C. 154(b) by 636 days.

(21) Appl. No.: 17/998,842

(22) PCT Filed: Jul. 9, 2021

(86) PCT No.: PCT/JP2021/025886

§ 371 (c)(1),
(2) Date: Nov. 15, 2022

(87) PCT Pub. No.: WO2022/009968

PCT Pub. Date: Jan. 13, 2022

(65) Prior Publication Data

US 2023/0251263 A1 Aug. 10, 2023

(30) Foreign Application Priority Data

Jul. 9, 2020 (JP) ................................ 2020-118613

(51) Int. Cl.
*G01N 33/574* (2006.01)
*C08F 216/18* (2006.01)
*G01N 33/575* (2026.01)

(52) U.S. Cl.
CPC ....... *G01N 33/5759* (2026.01); *C08F 216/18* (2013.01)

(58) Field of Classification Search
CPC ......................... G01N 33/574; G01N 33/5759
See application file for complete search history.

(56) References Cited

U.S. PATENT DOCUMENTS

| | | | |
|---|---|---|---|
| 9,372,136 B2 | 6/2016 | Kanbara et al. | |
| 10,444,233 B2 | 10/2019 | Tseng et al. | |
| 2014/0178890 A1* | 6/2014 | Kanbara ................ | G01N 1/405 435/6.14 |
| 2016/0291019 A1 | 10/2016 | Yoon et al. | |
| 2019/0091380 A1* | 3/2019 | Tanaka .................. | A61L 33/064 |
| 2021/0122867 A1 | 4/2021 | Nishiura | |
| 2021/0362100 A1 | 11/2021 | Nishiya et al. | |

FOREIGN PATENT DOCUMENTS

| | | | |
|---|---|---|---|
| CN | 111065454 | A | 4/2020 |
| EP | 3 647 389 | A1 | 5/2020 |
| EP | 3 875 170 | A1 | 9/2021 |
| JP | S60-228509 | A | 11/1985 |
| JP | H01-108202 | A | 4/1989 |
| JP | H01-108203 | A | 4/1989 |
| JP | H07-002805 | B2 | 1/1995 |
| JP | 3096494 | B2 | 10/2000 |
| JP | 2004-161954 | A | 6/2004 |
| JP | 2009-167282 | A | 7/2009 |
| JP | 2015-523100 | A | 8/2015 |
| JP | 2016-050266 | A | 4/2016 |
| WO | 2012/173097 | A1 | 12/2012 |

(Continued)

OTHER PUBLICATIONS

International Search Report and Written Opinion (Application No. PCT/JP2021/025886) dated Sep. 28, 2021.

(Continued)

*Primary Examiner* — Sarah Alawadi
(74) *Attorney, Agent, or Firm* — Muncy, Geissler, Olds & Lowe, P.C.

(57) ABSTRACT

[Problem to be Solved]

To provide a polymer material having cancer cell adhesion properties while having biocompatibility.

[Means to Solve the Problem]

A composition for cancer cell adhesion according to the present invention comprises a biocompatible copolymer comprising:

at least one repeating unit (A) represented by the following formula (1):

(1)

wherein $R^1$ represents a methyl group or an ethyl group; and at least one repeating unit (B) represented by the following formula (2):

(2)

wherein $R^2$ represents an aliphatic hydrocarbon group.

10 Claims, No Drawings

(56) References Cited

FOREIGN PATENT DOCUMENTS

| | | | |
|---|---|---|---|
| WO | 2014/196269 | A1 | 12/2014 |
| WO | 2017/150000 | A1 | 9/2017 |
| WO | 2019/003558 | A1 | 1/2019 |
| WO | 2020/138230 | A1 | 7/2020 |

OTHER PUBLICATIONS

English translation of the International Preliminary Report on Patentability (Chapter I) dated Jan. 19, 2023 (Application No. PCT/JP2021/025886).
Extended European Search Report (Application No. 21838414.7) dated Jun. 17, 2024 (6 pages).
Chinese Office Action (Application No. 202180030652.8) dated May 6, 2025 (with English translation) (14 pages).
Chinese Office Action (Application No. 202180030652.8) dated Oct. 28, 2025 (with English translation) (8 pages).

* cited by examiner

COMPOSITION FOR CANCER CELL ADHESION, CANCER CELL COLLECTION FILTER, AND METHOD FOR DETECTING CANCER CELL

BACKGROUND OF THE INVENTION

Field of the Invention

The present invention relates to a composition for cancer cell adhesion. The present invention also relates to a cancer cell collection filter having the composition for cancer cell adhesion. The present invention also relates to a method for detecting a cancer cell using the cancer cell collection filter.

Background Art

Conventionally, medical materials using various polymer materials have been studied. In medical materials, a synthetic material, which is a foreign substance for the living body, is used in contact with tissue or blood in the living body, and therefore, the material is required to have biocompatibility. As a biocompatible material, for example, poly(2-methoxyethyl acrylate) (PMEA) has been developed so far (see Patent Document 1). This PMEA is known to exhibit biocompatibility due to having so-called intermediate water (water in a state in which an exothermic peak resulting from low-temperature crystal formation of water is stably observed around −40° C. in a temperature increasing process from −100° C. in a differential scanning calorimeter measurement), which is considered to be water weakly bound to a polymer chain by interaction with the polymer chain.

Recently there has been proposed a copolymer of diethyleneglycol monoethyl monovinyl ether (EOEOVE) as a hydrophilic vinyl ether and n-butyl vinyl ether as a hydrophobic vinyl ether as biocompatible materials having an oxyethylene structure in the side chains and having intermediate water as in PMEA (see Patent Document 2). However, it has been shown that the adhesion to cancer cells is extremely low in this copolymer.

On the other hand, there is currently a need for a material having cancer cell adhesion properties while being a polymer material having biocompatibility for the detection of cancer cells.

PRIOR ART DOCUMENTS

Patent Documents

Patent Document 1: Japanese Patent Application Laid-Open Publication No. 2004-161954

Patent Document 2: International Publication No. 2017/150000

SUMMARY OF THE INVENTION

Problem to be Solved

Accordingly, it is an object of the present invention to provide a polymer material having cancer cell adhesion properties while having biocompatibility. It is also an object of the present invention to provide a cancer cell collection filter and a cancer cell detection method using the polymer material having cancer cell adhesion properties.

Means for Solving the Problem

As a result of intensive studies to solve the above-mentioned problems, the present inventors found that a copolymer comprising a specific repeating unit (A) derived from a specific hydrophilic vinyl ether other than diethyleneglycol monoethyl monovinyl ether (EOEOVE) and a repeating unit (B) derived from a specific hydrophobic vinyl ether has cancer cell adhesion properties while having biocompatibility, and thus completed the present invention.

That is, according to the present invention, the following invention is provided.

[1] A composition for cancer cell adhesion comprising a biocompatible copolymer comprising:

at least one repeating unit (A) represented by the following formula (1):

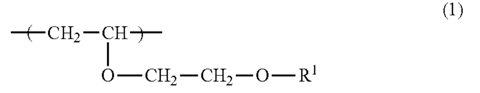

(1)

wherein $R^1$ represents a methyl group or an ethyl group; and at least one repeating unit (B) represented by the following formula (2):

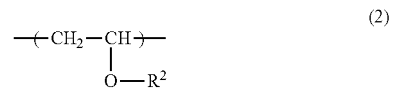

(2)

wherein $R^2$ represents an aliphatic hydrocarbon group.

[2] The composition for cancer cell adhesion according to [1], wherein the biocompatible copolymer is a random copolymer of segment A consisting of the repeating unit (A) and segment B consisting of the repeating unit (B).

[3] The composition for cancer cell adhesion according to [1] or [2], wherein the biocompatible copolymer has a composition ratio (molar ratio) of the repeating unit (A) to the repeating unit (B) of 90:10 to 10:90.

[4] The composition for cancer cell adhesion according to any one of [1] to [3], wherein $R^2$ in the repeating unit (B) of the biocompatible copolymer is a linear or branched alkyl group or alkenyl group having 2 to 10 carbon atoms, or a monocyclic or polycyclic alkyl group or alkenyl group having 3 to 20 carbon atoms.

[5] The composition for cancer cell adhesion according to any one of [1] to [3], wherein $R^2$ in the repeating unit (B) of the biocompatible copolymer is a linear or branched alkyl group having 2 to 10 carbon atoms.

[6] The composition for cancer cell adhesion according to any one of [1] to [5], wherein the ratio of the weight-average molecular weight (Mw) to the number-average molecular weight (Mn) of the biocompatible copolymer is 1.0 to 3.0.

[7] The composition for cancer cell adhesion according to any one of [1] to [6], wherein the number-average molecular weight (Mn) of the biocompatible copolymer is 3,000 to 30,000.

[8] A cancer cell collection filter wherein at least a part of the surface thereof includes the composition for cancer cell adhesion according to any one of [1] to [7].

[9] A method for detecting cancer cells, comprising the step of filtering blood using the cancer cell collection filter according to [8].

[10] The method for detecting cancer cells according to [9], further comprising the step of culturing the cancer cells collected in the filtering step.

Effect of the Invention

According to the present invention, it is possible to provide a polymer material having cancer cell adhesion while having biocompatibility. In addition, according to the present invention, it is possible to provide a cancer cell collection filter and a method for detecting cancer cells using the polymer material having cancer cell adhesion properties.

MODE FOR CARRYING OUT THE INVENTION

<Composition for Cancer Cell Adhesion>

A composition for cancer cell adhesion according to the present invention comprises a biocompatible copolymer containing at least one repeating unit (A) and at least one repeating unit (B).

(Biocompatible Copolymer)

The biocompatible copolymer according to the present invention contains at least one repeating unit (A) represented by the following formula (1):

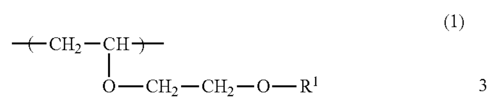
(1)

wherein $R^1$ represents a methyl group or an ethyl group; and at least one repeating unit (B) represented by the following formula at least one of the following formula (2):

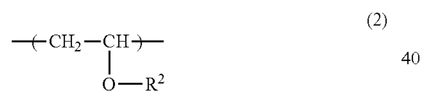
(2)

wherein $R^2$ represents an aliphatic hydrocarbon group.

Examples of the monomer that gives the repeating unit (A) of formula (1) include hydrophilic vinyl ethers represented by the following formula (3):

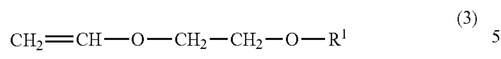
(3)

wherein $R^1$ is the same as $R^1$ in Formula (1).

More specifically, examples of the hydrophilic vinyl ether represented by formula (3) include 2-methoxyethyl vinyl ether (MOVE) and 2-ethoxyethyl vinyl ether (EOVE). Among these, MOVE is preferable because it has superior cancer cell adhesion properties.

Examples of the monomer that gives the repeating unit (B) include hydrophobic vinyl ethers represented by the following formula (4):

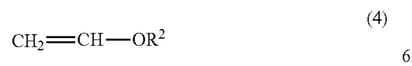
(4)

wherein $R^2$ is the same as $R^2$ in formula (2).

Here, $R^2$ is an aliphatic hydrocarbon group, specifically, a linear or branched alkyl group or alkenyl group, or a monocyclic or polycyclic alkyl group or alkenyl group.

The linear or branched alkyl group or alkenyl group preferably has 2 to 10 carbon atoms, more preferably 3 to 8 carbon atoms, and further preferably 4 to 6 carbon atoms.

Specific examples of the linear or branched alkyl groups or alkenyl groups include linear or branched alkyl groups such as an ethyl group, n-propyl group, isopropyl group, n-butyl group, isobutyl group, tert-butyl group, 1-pentyl group, 2-pentyl group, 3-pentyl group, 1-(2-methyl)-butyl group, 2-(2-methyl)-butyl group, 1-(3-methyl)-butyl group, 2-(3-methyl)-butyl group, (2,2-dimethyl)-propyl group, 1-hexyl group, 2-hexyl group, 3-hexyl group, 1-heptyl group, 2-heptyl group, 3-heptyl group, 4-heptyl group, 1-octyl group, 1-(2-ethyl)-hexyl group; and linear or branched alkenyl groups such as a vinyl group, 1-propenyl group, allyl group, 2-butenyl group, 3-butenyl group, isopropenyl group, isobutenyl group, 1-pentenyl group, 2-pentenyl group, 3-pentenyl group, 4-pentenyl group, 1-hexenyl group, 2-hexenyl group, 3-hexenyl group, 4-hexenyl group, and 5-hexenyl group.

The monocyclic or polycyclic alkyl group or alkenyl group preferably has 3 to 20 carbon atoms, more preferably 4 to 15 carbon atoms, and further preferably 5 to 12 carbon atoms.

Specific examples of the monocyclic or polycyclic alkyl group or alkenyl group include monocyclic alkyl groups or alkenyl groups such as a cyclopentyl group, cyclopentylmethyl group, methylcyclopentyl group, dimethylcyclopentyl group, cyclohexyl group, cyclohexylmethyl group, methylcyclohexyl group, dimethylcyclohexyl group, cyclohexenyl group, cycloheptyl group, cyclooctyl group, cyclononyl group, cyclodecyl group, cycloundecyl group, cyclododecyl group, cyclotridecyl group, cyclotetradecyl group, cyclopentadecyl group, cyclooctadecyl group, and cycloicosyl group; and polycyclic alkyl groups or alkenyl groups such as a bicyclohexyl group, decahydronaphthyl group, norbornyl group, methylnorbornyl group, isobornyl group, group, adamantyl tricyclodecanyl group, tricyclodecenyl group, tetracyclododecyl group, and the like.

Among these aliphatic hydrocarbon groups, linear or branched alkyl groups are preferred. More specifically, preferred as the hydrophobic vinyl ether represented by formula (4) are n-butyl vinyl ether (NBVE) and 2-ethylhexyl vinyl ether (EHVE). Among these, NBVE is preferred because it has superior cancer cell adhesion properties.

The composition ratio (molar ratio) of the repeating unit (A) to the repeating unit (B) in the biocompatible copolymer of the present invention (hereinafter referred to as "copolymer") is preferably in the range of 90:10 to 10:90, more preferably in the range of 85:15 to 15:85, and particularly preferably in the range of 80:20 to 20:80.

As for the molecular weight of the copolymer in the present invention, for example, the number average molecular weight (Mn) obtained from a standard polystyrene calibration curve by gel permeation chromatography (GPC) is preferably 1,000 to 100,000, more preferably 2,000 to 50,000, and further preferably 3,000 to 30,000. When the Mn is within the above-mentioned range, the adhesion property of the cancer cells is more excellent in the copolymer.

The ratio of the weight average molecular weight (Mw) to the number average molecular weight (Mn) (molecular weight distribution, Mw/Mn) of the copolymer in the present invention is preferably 1.0 to 3.0, more preferably 1.0 to 2.0, further preferably 1.0 to 1.5, and further more preferably 1.0 to 1.3. When the molecular weight distribution (Mw/Mn) is within the above-described range, the copolymer has better adhesion to cancer cells.

The copolymer in the present invention may be either a random copolymer or a block copolymer, but from the viewpoint of adhesion of cancer cells, a random copolymer is preferable containing segment A consisting of repeating unit (A) and segment B consisting of repeating unit (B). The composition distribution of segment A and segment B in the random copolymer is not particularly limited, and for example, a full random copolymer close to a statistically random composition, a taper (gradient) copolymer with a gradient in the composition distribution can be mentioned. Since the copolymer is a random copolymer, sufficient adhesion to cancer cells can be obtained without depending on the molecular weight.

The copolymer of the present invention can be prepared by polymerizing a hydrophilic vinyl ether represented by formula (3) above and a hydrophobic vinyl ether (4) represented by formula (4) above according to an ordinary method. In order to obtain a copolymer having a desired composition ratio and molecular weight with good reproducibility, living cationic polymerization is particularly preferred as the polymerization method. In the living cationic polymerization method, since the molecular weight of the copolymer is almost uniquely determined by the molar ratio of the monomer to the polymerization initiator, the molecular weight of the copolymer can be arbitrarily controlled over a wide range by changing the amount of the monomer and the polymerization initiator used.

The polymerization initiator used in the polymerization of the copolymer is not particularly limited as long as it allows the cationic polymerization to proceed in a living manner, and preferred for use as a living cationic polymerization initiator of vinyl ethers include an HI/12 type initiator (for example, Japanese Patent Laid-Open Publication No. S60-228509), a polymerization initiator in which a Lewis acid catalyst (such as an organoaluminum compound) is combined with an additive such as a base (such as an ether) (for example, specification of Japanese Patent No. 3096494, Japanese Patent Laid-Open Publication No. H7-2805, Japanese Patent Laid-Open Publication No. S62-257910, Japanese Patent Laid-Open Publication Nos. H1-108202 and H1-108203) and the like.

The amount of the polymerization initiator used is preferably 0.001 to 20 mol %, more preferably 0.01 to 10 mol %, particularly preferably 1 mol % or less, with respect to the total amount of the raw material monomer.

The living cationic polymerization reaction is preferably carried out in the presence of a suitable organic solvent, but may also be carried out in the absence thereof. Examples of the organic solvent which can be used include aromatic hydrocarbon solvents such as benzene, toluene and xylene; aliphatic hydrocarbon solvents such as propane, n-butane, isobutane, n-pentane, isopentane, n-hexane, n-heptane, n-octane, isooctane, decane, hexadecane and cyclohexane; halogenated hydrocarbon solvents such as methylene chloride, ethylene chloride, and carbon tetrachloride; and ether solvents such as diethyl ether, dibutyl ether, tetrahydrofuran (THF), dioxane and ethylene glycol diethyl ether. These organic solvents may be used alone or in combination of two or more thereof, if necessary. Among these organic solvents, a hydrocarbon solvent such as an aromatic hydrocarbon solvent or an aliphatic hydrocarbon solvent is preferable, and toluene or cyclohexane is particularly preferable.

The polymerization temperature in this polymerization reaction is usually −80 to 150° C., preferably −50 to 100° C. and particularly preferably −20 to 80° C., although it varies depending on the type of polymerization initiator, monomer and solvent used. The polymerization time is usually about 10 minutes to 100 hours, although it varies depending on the type of polymerization initiator, monomer, solvent and reaction temperature and reaction temperature used. The polymerization reaction may be carried out in a batch or continuous manner. After the polymerization reaction, if necessary, purification may be carried out by a known method in order to remove the unreacted monomer.

<Cancer Cell Collection Filter>

A cancer cell collection filter of the present invention (hereinafter referred to simply as "a filter") has the above-described composition for cancer cell adhesion on at least a part of its surface, and cancer cells in the blood can be collected by filtering the blood with the filter. The filter is not particularly limited as long as it is a filter for blood filtration, and a well-known filter can be used. Although the filter may have a composition for cancer cell adhesion on at least a part of its surface, it is preferable that 50% or more of the entire surface area on the side in contact with the blood to be filtered is covered with the composition for cancer cell adhesion, more preferably 80% or more is covered, and further preferably, the entire surface area on the side in contact with the blood to be filtered is covered with the composition for cancer cell adhesion.

From the viewpoint of collecting cancer cells more efficiently, the average pore size of the through-hole is preferably 5 to 30 μm, more preferably 5 to 15 μm, and further preferably 5 to 10 μm.

The average opening ratio of the filter is preferably 5 to 50%, more preferably 10 to 40%, and further preferably 20 to 40%. Here, the average opening ratio of the filter means the ratio of an area of the through-holes to an area of the entire filter.

As a method for retaining the above-mentioned composition for cancer cell adhesion on the surface of a filter, various methods can be used, such as a method of coating the surface of the filter with the composition for cancer cell adhesion, a method of bonding the surface of a filter with a biocompatible polymer using active energy ray such as radiation, electron beam, ultraviolet ray, or the like, and a method of bonding by reacting a functional group on the surface of a filter with a composition for cancer cell adhesion. In the case where a coating method is used, any of a method such as an application method, spraying method, dipping method and the like may be used as the method for coating the composition for cancer cell adhesion. The coating is performed by attaching the composition for cancer cell adhesion to the substrate surface by a dipping method, a spraying method, a spin coating method or the like, and then removing (drying) the solvent. The film thickness after drying is preferably 0.01 μm to 1.0 mm, more preferably 0.1 to 100 μm, and further preferably 0.5 to 50 μm. When the film thickness is within the above-mentioned ranges, adhesion properties of cancer cells can be sufficiently expressed.

In order to fix the composition for cancer cell adhesion more firmly to the substrate, heat may be applied to the substrate after the composition for cancer cell adhesion is coated. In addition, a biocompatible polymer may be crosslinked. Examples of the crosslinking method include a method in which a crosslinking monomer is added to a material of a polymer in advance. Electron beam, γ-ray, or light irradiation may be used for crosslinking.

The material and shape of the filter are not particularly limited, and for example, porous materials, fibers, nonwoven fabrics, films, sheets and tubes can be used.

Examples of the material of the substrate include natural polymers such as cotton and hemp, nylon, polyester, polyacrylonitrile, halogenated polyolefin, polyurethane, polyamide, polysulfone, polyethersulfone, poly(meth)acrylate, synthetic polymers such as halogenated polyolefin ethylene-polyvinyl alcohol copolymer, butadiene-acrylonitrile copolymer, and mixtures thereof. Mention can also be made to metals, ceramics, composite materials thereof, and the like, and the filter may be formed of a plurality of substrates.

The above-mentioned metals are not particularly limited, and for example, noble metals such as gold and silver, poor metals such as copper, aluminum, tungsten, nickel, chromium and titanium, and alloys of these metals can be used. The metal may be used alone or as an alloy with other metals or as an oxide of the metal in order to impart functionality. From the viewpoint of cost and availability, it is preferable to use nickel, copper, or a metal mainly composed of these metals. Here, the main component refers to a component which accounts for 50% by weight or more of the material forming the substrate. It is also possible to form through holes in these metals by a method such as photolithography to form a screen filter.

<Detection Method of Cancer Cell>

The method for detecting cancer cells of the present invention includes a step of filtering blood with the above-described cancer cell collection filter, and preferably further includes a step of culturing cancer cells collected in the filtering step. Each step will be described in details below.

(Filtration Step)

In a cancer cell detection method, cancer cells in the blood can be collected at a high collection rate by filtering the blood with a filter. As an example of a method of filtering the blood with a filter, for example, mention can be made to a method in which a filter is installed in a flow path through which the blood circulates to filter the blood. In such a method, blood pooled in bone marrow, spleen, liver and the like, blood such as umbilical cord blood, also lymph, tissue fluid and the like can be used as samples, but it is most convenient to use peripheral blood circulating in the body. Detection of the presence of circulating cancer cells (hereinafter referred to as "CTC") in peripheral blood is a useful means for judging the progress of the disease state of cancer.

When the presence of cancer cells is detected by a method of filtering blood by installing a filter in the flow path through which the blood circulates, this can be carried out by, for example, incorporating a filter into the flow path, introducing peripheral blood into the flow path to collect cells containing CTC, and confirming whether or not CTC is present in the collected cells. Examples of the method of introducing blood into the flow path include a method of using pressure from the inlet direction of the flow path, a method of using pressure reduction from the outlet direction of the flow path, and a method of using a peristaltic pump. In addition, when CTC is concentrated from, for example, 1 mL of blood, the area of the filter to be used is preferably 1 to 10 $cm^2$.

When CTC is collected by the above method, not only CTC but also blood cells such as white blood cells are collected at the same time. Therefore, it is necessary to confirm whether or not cancer cells are contained in the collected cells. For example, after collecting CTC by the above-described method, cells can be stained with an antibody against a fluorescence-labeled cancer marker to confirm that the cells are cancer cells. As an antibody against a cancer marker, an anti-EpCAM antibody or the like can be exemplified.

It is also possible to confirm that the cell is a cancer cell by analyzing the genes of the cell collected by the method described above. For example, it is possible to confirm that the cell is a cancer cell by analyzing mutations in genes such as p53, K-RAS, H-RAS, N-RAS, BRAF, and APC. The results of these genetic analyses can also be used to determine the treatment policy of the patient. Alternatively, it is possible to confirm that the cell is a cancer cell by measuring the telomerase activity or the like of the cell collected by the above-described method.

(Culturing Step)

The method for detecting cancer cells can also detect a trace amount of cancer cells by further including a step of culturing the cancer cells. The method for culturing the cancer cells is not particularly limited, and a method generally used for culturing cells can be used.

EXAMPLES

Next, the present invention will be described in more details with reference to the Examples and Comparative Examples, but the present invention shall not be limited to these Examples.

In the Examples, the composition ratio of the copolymer was determined from the result of 1H NMR analysis, and the weight average molecular weight (Mw), number average molecular weight (Mn), and molecular weight distribution (Mw/Mn) were determined from the result of GPC molecular weight analysis (in terms of polystyrene). The analysis apparatus and measurement conditions are as follows.

(NMR Measurement Conditions)

Apparatus: Model Number: AL-400, manufactured by JEOL

Solvent: deuterated chloroform

Measuring temperature: 30° C.

(Measurement Conditions of GPC)

Apparatus: "HLC-8320 GPC", manufactured by Tosoh Corporation

Detector: RI detector

Mobile phase: tetrahydrofuran

Flow rate: 1 mL/min

Column: "Shodex LF-804"×3, made by Showa Denko K.K.

Column Temperature: 40° C.

Example 1

Synthesis A of 2-methoxyethyl Vinyl Ether/n-butyl Vinyl Ether Random Copolymer (MOVE-ran-NBVE)

76.0 mL of toluene as a solvent, 32.6 mL of ethyl acetate as an additive base, 2.3 mL of 2-methoxyethyl vinyl ether (MOVE) as a hydrophilic vinyl ether, 10.3 mL of n-butyl vinyl ether (NBVE) as a hydrophobic vinyl ether and 494.0 μL of 1-isobutoxyethyl acetate (IBEA) as a starting species were added to a Schlenk tube with a three way stopcock, which was heat-dehydrated at 300° C. or more for 10 minutes under a dry nitrogen atmosphere, and stirred well.

Next, the temperature was maintained at 0° C., 0.93M (3.7 mL) of $Et_{1.5}AlCl_{1.5}$ was added as a Lewis acid catalyst to initiate polymerization, and the reaction was carried out for 90 minutes.

Polymerization was stopped with methanol containing a small amount of sodium methoxide (1M). To the stopped solution was added 3 g of ion exchange resin (product name: Amberlyst MSPS2-1. DRY, manufactured by Organo Corp.), and the mixture was stirred overnight. Then, the solution was passed through celite and a filter having a pore size of 1 μm. The solvent was evaporated and then dried under reduced pressure to obtain the desired random copolymer A. The composition ratio, weight average molecular weight (Mw), number average molecular weight (Mn), and molecular weight distribution (Mw/Mn) of the random copolymer A thus obtained are shown in Table 1.

Example 2

Synthesis B of 2-methoxyethyl Vinyl Ether/n-butyl Vinyl Ether Random Copolymer (MOVE-ran-NBVE)

Random copolymer B was obtained by the same procedure as in Example 1 except that the addition amount of IBEA was changed to 185.0 μL. The composition ratio, weight average molecular weight (Mw), number average molecular weight (Mn), and molecular weight distribution (Mw/Mn) of the random copolymer B thus obtained are shown in Table 1.

Example 3

Synthesis C of 2-methoxyethyl Vinyl Ether/n-butyl Vinyl Ether Random Copolymer (MOVE-ran-NBVE)

Random copolymer C was obtained by the same procedure as in Example 1 except that 9.3 mL of MOVE was added as a hydrophilic vinyl ether, 2.6 mL of NBVE was added as a hydrophobic vinyl ether, and 300.0 μL of IBEA was added as a starting species. The composition ratio, weight average molecular weight (Mw), number average molecular weight (Mn) Mn), and molecular weight distribution (Mw/Mn) of the random copolymer C thus obtained are shown in Table 1.

Example 4

Synthesis D of 2-methoxyethyl Vinyl Ether/n-butyl Vinyl Ether Random Copolymer (MOVE-ran-NBVE)

Random copolymer D was obtained by the same procedure as in Example 1, except that 5.8 mL of MOVE was added as a hydrophilic vinyl ether, 6.4 mL of NBVE was added as a hydrophobic vinyl ether, and 300.0 μL of IBE was added as a starting species. The composition ratio, weight average molecular weight (Mw), number average molecular weight (Mn), and molecular weight distribution (Mw/Mn) of the random copolymer D thus obtained are shown in Table 1.

Example 5

Synthesis E of 2-ethoxyethyl Vinyl Ether/n-butyl Vinyl Ether Random Copolymer (EOVE-ran-NBVE)

Random copolymer E was obtained by the same procedure as in Example 1, except that 7.3 mL of 2-ethoxyethyl vinyl ether (EOVE) was added as a hydrophilic vinyl ether, 6.4 mL of NBVE was added as a hydrophobic vinyl ether, and 300.0 μL of IBEA was added as a starting species. The composition ratio, weight average molecular weight (Mw), number average molecular weight (Mn), and molecular weight distribution (Mw/Mn) of the random copolymer E thus obtained are shown in Table 1.

Example 6

Synthesis F of 2-methoxyethyl Vinyl Ether/2-ethyl Hexyl Vinyl Ether Random Copolymer (MOVE-ran-EHVE)

Random copolymer F was obtained by the same procedure as in Example 1, except that 5.8 mL of MOVE was added as a hydrophilic vinyl ether, 8.0 mL of 2-ethylhexyl vinyl ether (EHVE) was added as a hydrophobic vinyl ether, and 300.0 μL of IBEA was added as a starting species. The composition ratio, weight average molecular weight (Mw), number average molecular weight (Mn), and molecular weight distribution (Mw/Mn) of the random copolymer F thus obtained are shown in Table 1.

Example 7

Synthesis G of 2-methoxyethyl Vinyl Ether/n-butyl Vinyl Ether Random Copolymer (MOVE-ran-NBVE)

Random copolymer G was obtained by the same procedure as in Example 4 except that the addition amount of IBEA was changed to 74.0 μL. The composition ratio, weight average molecular weight (Mw), number average molecular weight (Mn), and molecular weight distribution (MwMn) of the random copolymer G thus obtained are shown in Table 1.

Comparative Example 1

Synthesis H of Poly(n-butyl Vinyl Ether) (PNBVE)

Homopolymer H was obtained by the same procedure as in Example 1 except that no hydrophilic vinyl ether was added and 12.9 mL of NBVE was added as a hydrophobic vinyl ether and 300.0 μL of IBE was added as a starting species. The weight average molecular weight (Mw), number average molecular weight (Mn), and molecular weight distribution (Mw/Mn) of the homopolymer H thus obtained are shown in Table 1.

Comparative Example 2

Synthesis I of Poly(2-methoxyethyl Acrylate) (PMEA)

15.00 g of 2-methoxyethyl acrylate (MEA) as a monomer was dissolved in 60.23 g of 1,4-dioxane and bubbled with argon gas for 30 minutes. Then, 15.03 mg of 2,2'-azobisisobutyronitrile (AIBN) was added as a starting species, and polymerization was carried out at 75° C. for 6 hours while bubbling with argon gas. A polymerization solution of the generated polymer was dropped into 1 L of n-hexane to collect the polymer as a precipitate, and the precipitate was purified by repeating the precipitation operation 3 times in a THF/n-hexane system. After the precipitation operation, the precipitate was contacted with pure water for 24 hours or more and stirred to remove substances eluted in the water, and then the solvent was removed by an evaporator and vacuum drying (at 40° C. for 72 hours or more). Homopolymer I was obtained as the final product. The weight average molecular weight (Mw), number average molecular weight (Mn) and molecular weight distribution (Mw/Mn) of the homopolymer I thus obtained are shown in Table 1.

Comparative Example 3

Synthesis J of Diethylene Glycol Monoethyl Monovinyl Ether/n-butyl Vinyl Ether Random Copolymer (EOEOVE-ran-NBVE)

181.0 ml of toluene as a solvent, 76.4 mL of ethyl acetate as an additive base, 4.0 mL of diethylene glycol monoethyl monovinyl ether (EOEOVE) as a hydrophilic vinyl ether, 28.2 mL of N-butyl vinyl ether (NBVE) as a hydrophobic vinyl ether, and 4 mM (450.0 μL) of an acetic acid adduct of isobutyl vinyl ether as a starting species were added to a 300 mL three neck flask with a three way stopcock, which was heated and dehydrated at 300° C. or more for 10 minutes under a dry nitrogen atmosphere, and the mixture was stirred well.

Next, the temperature was maintained at 0° C., and 8 mM (8.8 mL) of $Et_{1.5}AlCl_{1.5}$ was added as a Lewis acid catalyst to start polymerization, and the reaction was carried out for 90 minutes.

Polymerization was stopped with methanol containing a small amount of sodium methoxide (1M). To the stopped solution was added 5% by mass of ion-exchange resin (product name: Amberlyst MSPS2-1. DRY, manufactured by Organo Corporation), and the mixture was stirred at room temperature for 1 hour. Then, the solution was passed through a celite and a filter having a pore size of 1 μm. The solvent was evaporated and then dried under reduced pressure to obtain the desired random copolymer J. The composition ratio, weight average molecular weight (Mw), number average molecular weight (Mn), and molecular weight distribution (Mw/Mn) of the random copolymer J thus obtained are shown in Table 1.

[Evaluation Test]

<Platelet Adhesion Test>

In order to examine blood compatibility, a platelet adhesion test was performed on polyethylene terephthalate (PET) plates which are surface-coated with the above-synthesized polymers A to J (Examples 1 to 7 and Comparative Examples 1 to 3).

Surface coating of the PET plates with each polymer was carried out by spin coating the PET plate surfaces with a 1.0 wt % ethanol solution of each polymer.

Human whole blood for experiments, purchased from the United States of America, was brought to room temperature prior to the experiment and centrifuged at 400 rcf for 5 minutes with a centrifuge. Approximately 0.5 mL of the supernatant was collected at this time and was used as platelet rich plasma (PRP). Thereafter, centrifugation was further performed at 2500 rcf for 10 minutes. At this time, approximately 2 mL of the supernatant was collected and was used as platelet poor plasma (PPP). A platelet suspension was prepared by diluting PRP with PPP so as to obtain a seeding density of $4.0\times10^7$ cells/$cm^2$. 0.2 mL of the prepared platelet suspension was dropped with a pipette onto PET plates that are surface-coated with each polymer and uncoated PET plates (blank) which were then left to stand at 37° C. for 60 minutes. Subsequently, they were rinsed with a phosphate buffer solution and incubated with a 1% glutaraldehyde solution at 37° C. for 120 minutes to fix the adhered platelets. Then washing was done with phosphate buffer saline and water and drying was done for 2 days or more in a vessel containing silica gel. After drying, the surfaces of the samples were observed with a scanning electron microscope and the platelet count adhering to an area of $1\times10^5$ $\mu m^2$ was measured. When the number of platelets adhering to a PET plate without coating (blank) was set to 1, the relative numbers of platelets adhering to each of the Examples and Comparative Examples were evaluated according to the following standards. The evaluation results are shown in Table 1.

(Evaluation Criteria)):

◎: Platelet adhesion number was less than 0.1.

○: Platelet adhesion number was 0.1 or more and less than 0.2.

x: Platelet adhesion number was 0.2 or more.

<Cancer Cell Adhesion Test>

In order to examine the adhesion property of cancer cells, an adhesion test of cancer cells was performed on polyethylene terephthalate (PET) plates which were surface-coated with each of the above-synthesized polymers A to G, I and J (Examples 1 to 7 and Comparative Examples 2 and 3). Since the polymer H had a large number of platelet adhesion and poor blood compatibility, it was not tested for the cancer cell adhesion test.

In the same manner as in the platelet adhesion test described above, PET plates that are surface-coated with each polymer and uncoated PET plates (blank) were prepared. Each of the prepared PET plates was placed in 24 wells (base area: 1.9 $cm^2$), and 1.0 mL of a cancer cell suspension (adjusted to a seeding density of 10,000/$cm^2$ in a medium containing 10% serum) was dropped onto each PET plate in each well by a pipette, and the plates were left to stand at 37° C. for 60 minutes. As the cancer cells, human fibrosarcoma cell lines HT-1080 and SW480 were used. The plates were then rinsed with phosphate buffered saline and the number of cancer cells adhering to the sample surfaces was counted. To facilitate the counting, the cells were fixed with 4% paraformaldehyde, and the cell nuclei were stained with 4',6-diamino-2-phenylindole (DAPI) and F-actin with phalloidin labeled with Alexa Fluor 488, then cell nuclei were counted using an all-in-one fluorescence microscope (KEYENCE, BZ-X710) to determine as the number of cancer cells. The relative number of cancer cells adhered to each of the Examples and Comparative Examples was evaluated based on the following criteria when the number of cancer cells adhered to a PET plate (blank) without coating was set to 1. The evaluation results are shown in Table 1. Since the polymer J had no adhesion properties to HT-1080, it was not tested for the adhesion test to SW480.

(Evaluation Criteria)

◎: Adhesion number of cancer cells was more than 3.0.

○: Adhesion number of cancer cells was more than 2.5 and 3.0 or less.

Δ: Adhesion number of cancer cells was more than 1.0 and 2.5 or less.

x: Adhesion number of cancer cells was 1.0 or less.

TABLE 1

| | Polymer | | | | | | Evaluation Test | | |
|---|---|---|---|---|---|---|---|---|---|
| | Segment A (Hydrophillic part) | Segment B (Hydrophobic part) | Hydrophillic part: Hydrophobic part | Mw | Mn | Mw/Mn | Platelet Adhesion Test | Cancer Cell Adhesion Test HT-1080 | SW480 |
| Ex. 1 | MOVE | NBVE | 20:80 | 5300 | 4700 | 1.13 | ◎ (0.000) | ◎ (5.0 or more) | ◎ (5.0 or more) |
| Ex. 2 | MOVE | NBVE | 20:80 | 12500 | 11300 | 1.11 | ◎ (0.000) | ◎ (5.0 or more) | ◎ (5.0 or more) |
| Ex. 3 | MOVE | NBVE | 80:20 | 8700 | 7900 | 1.10 | ◎ (0.017) | ◎ (3.5) | ◎ (3.2) |
| Ex. 4 | MOVE | NBVE | 50:50 | 8500 | 7200 | 1.18 | ○ (0.103) | ◎ (3.3) | ◎ (3.1) |
| Ex. 5 | EOVE | NBVE | 50:50 | 9400 | 8200 | 1.15 | ◎ (0.026) | ○ (2.8) | ○ (2.8) |
| Ex. 6 | MOVE | EHVE | 50:50 | 8800 | 8000 | 1.10 | ◎ (0.041) | ○ (3.0) | ◎ 4.1 |
| Ex. 7 | MOVE | NBVE | 50:50 | 24000 | 21600 | 1.11 | ◎ (0.019) | ◎ (3.9) | ◎ (4.3) |
| Comp. Ex. 1 | — | NBVE | — | 8500 | 7700 | 1.10 | × (0.202) | — | — |
| Comp. Ex. 2 | — | — | — | 103300 | 31000 | 3.33 | ◎ (0.010) | ○ (3.0) | Δ (2.4) |
| Comp. Ex. 3 | EOEOVE | NBVE | 10:90 | 3400 | 2400 | 1.43 | ◎ (0.033) | × (less than 0.1) | — |

The invention claimed is:

1. A method of detecting cancer cells, comprising:

adhering a biocompatible copolymer to the cancer cells, wherein the biocompatible copolymer comprises:

at least one repeating unit (A) represented by the following formula (1):

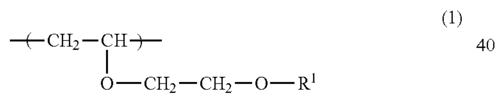

(1)

wherein $R^1$ represents a methyl group or an ethyl group; and at least one repeating unit (B) represented by the following formula (2):

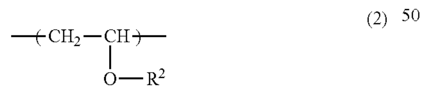

(2)

wherein $R^2$ represents an aliphatic hydrocarbon group.

2. The method according to claim 1, wherein the biocompatible copolymer is a random copolymer of segment A consisting of the repeating unit (A) and segment B consisting of the repeating unit (B).

3. The method according to claim 1, wherein the biocompatible copolymer has a composition ratio (molar ratio) of the repeating unit (A) to the repeating unit (B) of 90:10 to 10:90.

4. The method according to claim 1, wherein $R^2$ in the repeating unit (B) of the biocompatible copolymer is a linear or branched alkyl group or alkenyl group having 2 to 10 carbon atoms, or a monocyclic or polycyclic alkyl group or alkenyl group having 3 to 20 carbon atoms.

5. The method according to claim 1, wherein $R^2$ in the repeating unit (B) of the biocompatible copolymer is a linear or branched alkyl group having 2 to 10 carbon atoms.

6. The method according to claim 1, wherein the ratio of the weight-average molecular weight (Mw) to the number-average molecular weight (Mn) of the biocompatible copolymer is 1.0 to 3.0.

7. The method according to claim 1, wherein the number-average molecular weight (Mn) of the biocompatible copolymer is 3,000 to 30,000.

8. A method of detecting cancer cells by using a collection filter comprising:

adhering a biocompatible copolymer which is formed on a part of a surface of the collection filter to the cancer cells, wherein the biocompatible copolymer comprises:

at least one repeating unit (A) represented by the following formula (1);

(1)

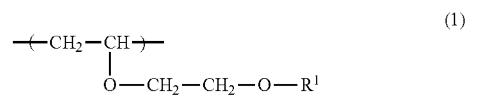

wherein $R^1$ represents a methyl group or an ethyl group; and at least one repeating unit (B) represented by the following formula (2):

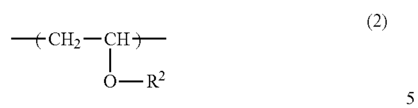
(2)
wherein
$R^2$ represents an aliphatic hydrocarbon group.
9. The method according to claim 8, further comprising the step of filtering blood using the collection filter.
10. The method according to claim 9, further comprising the step of culturing the cancer cells collected in the filtering step.
* * * * *